United States Patent
Scott et al.

(10) Patent No.: US 9,962,313 B2
(45) Date of Patent: May 8, 2018

(54) COMPRESSION GARMENT AND METHOD OF FORMING THE SAME

(71) Applicants: Ronald G. Scott, Plano, TX (US); Jimmy D. Laferney, Frisco, TX (US)

(72) Inventors: Ronald G. Scott, Plano, TX (US); Jimmy D. Laferney, Frisco, TX (US)

(73) Assignee: Ronald G. Scott, LLC, The Colony, TX (US)

( * ) Notice: Subject to any disclaimer, the term of this patent is extended or adjusted under 35 U.S.C. 154(b) by 440 days.

(21) Appl. No.: 14/618,335

(22) Filed: Feb. 10, 2015

(65) Prior Publication Data
US 2015/0224011 A1 Aug. 13, 2015

Related U.S. Application Data

(60) Provisional application No. 61/938,659, filed on Feb. 11, 2014.

(51) Int. Cl.
*A61H 7/00* (2006.01)
*A61F 13/08* (2006.01)

(52) U.S. Cl.
CPC .......... *A61H 7/001* (2013.01); *A61F 13/08* (2013.01); *A61H 2201/0184* (2013.01); *A61H 2201/1207* (2013.01); *A61H 2201/164* (2013.01); *A61H 2201/165* (2013.01); *A61H 2201/5002* (2013.01); *A61H 2201/5007* (2013.01); *A61H 2201/5061* (2013.01); *A61H 2209/00* (2013.01)

(58) Field of Classification Search
CPC .......... A61H 7/00–7/001; A61H 11/00–11/02; A61H 2209/00; A61H 2201/164; A61H 2201/1207; A61H 2201/5002; A61H 2201/5007; A61H 2201/5061; A61H 2201/5071; A61H 2205/10; A61F 13/08–13/085; A61F 2013/0028
See application file for complete search history.

(56) References Cited

U.S. PATENT DOCUMENTS

| | | | | |
|---|---|---|---|---|
| 7,213,420 B2 * | 5/2007 | Lynch | .................. | A41B 11/005 66/186 |
| 2007/0210011 A1 * | 9/2007 | Hook | ..................... | B01D 39/08 210/767 |
| 2010/0275338 A1 * | 11/2010 | Hyde | ................... | A61B 5/1077 2/69 |
| 2011/0066091 A1 * | 3/2011 | Larson | ............... | A61B 17/1325 601/134 |
| 2012/0089063 A1 * | 4/2012 | Olson | .................. | A61H 9/0078 601/152 |
| 2014/0081187 A1 * | 3/2014 | Wyatt | ................... | A61H 7/007 601/152 |

* cited by examiner

Primary Examiner — Rachel T Sippel
(74) Attorney, Agent, or Firm — International IP Law Group, PLLC

(57) ABSTRACT

A compression garment and methods of forming and operating the same. In one embodiment, the compression garment includes an electrically stimulated auxetic material having a dimension responsive to an electrical signal, an electrical contact coupled to the electrically stimulated auxetic material and an electrical power source. The compression garment also includes a controller, coupled to the electrical contact and the electrical power source, configured to provide the electrical signal to control a pressure produced by the compression garment via the electrically stimulated auxetic material.

20 Claims, 3 Drawing Sheets

COMPRESSION GARMENT AND METHOD OF FORMING THE SAME

CROSS-REFERENCE TO RELATED APPLICATIONS

This application claims priority to and the benefit of U.S. Provisional Application No. 61/938,659, entitled "COMPRESSION GARMENT AND METHOD OF FORMING THE SAME," filed Feb. 11, 2014, the entire disclosure of which is hereby incorporated herein by reference.

TECHNICAL FIELD

The present invention is directed, in general, to compression garments and, more specifically, to a compression garment formed with an electrically stimulated auxetic material and method of forming the same.

BACKGROUND

Patients with non-healing wounds generally present a clinical condition with insufficient venous drainage in the patient's extremities such as in the legs. Cornerstone medical therapy for insufficient venous drainage is compression therapy, wherein a tight-fitting garment such as a stocking is worn over the extremity, or a wrapped bandage is applied to an affected area such as around the head. A conventional practice of compression therapy has been the use of compression stockings, which can be obtained in two pressure classes. One pressure class of compression garments, such as stockings, provides an external pressure to an extremity such as a leg with a pressure on an affected area up to 20 millimeters ("mm") of mercury ("Hg"). The stockings can be obtained over-the-counter from a pharmacy without a physician's prescription. Another class of compression stockings provides an external pressure equal to or greater than 20 mm of Hg, and requires a physician's prescription. Prescribed compression stockings are obtainable in incremental pressure gradations of 10 mm of Hg.

A conventional compression stocking is generally designed with an elastic material that provides an initial pressure. The pressure produced and maintained by the stocking is not verifiable over time, however, particularly after periodic use and washing. A conventional compression garment frequently has a short useful life. Examples of conventional compression garments include Jobst™ stockings (compression garments), Unna™ paste boots, multi-layer wrapping systems, and various compression wraps.

A problem with conventional compression garments such as compression stockings is that patients under a physician's care are generally elderly, obese, arthritic, poorly conditioned, and may suffer from poor vision and/or a lack of coordination. The net result is the patient is frequently unable to put on a compression stocking without assistance, particularly when there are other comorbidities.

A compression garment improperly applied, such as with too much pressure or with unintended folds, can cause trauma to the patient's skin, particularly in an elderly or otherwise compromised patient. A compression garment with too tight of a fit can produce pressure ulcers comparable to bed sores. Conversely, a garment with reduced pressure is easier to put on, but does not provide a pressure necessary for a patient's treatment.

A problem with the current treatment of venous insufficiency includes patients not wearing compression garments due to inability to don and doff the garments easily. Another problem is the need to wear multi-layer and paste boots for a week at a time, which precludes many normal activities. Excessive heat generation, morbidity in obese and frail patients, atrophic members in patients, and patients with thin-skin and arthritis complicating the patient's ability to perform self-care are further concerns with the current treatment of venous insufficiency.

To illustrate the extent of venous disease in the United States, roughly 10 times more people suffer with venous disease than with arterial disease. At the present time, about 6,000,000 Americans have associated skin changes, and 500,000 Americans exhibit skin ulcers from underlying venous disease. In a typical year, about 600,000 Americans are hospitalized with venous disease issues. Chronic venous-lymphatic insufficiencies cause varicose veins, painful leg edema, chronic disfiguring skin changes, and difficult-to-heal ulcers. The compression garment industry to treat such patients is a multi-billion dollar industry worldwide.

Limitations of conventional processes to construct compression have now become substantial hindrances for reliable treatment of venous insufficiency. No satisfactory strategy has emerged to provide a reliable solution to provide a repeatable and controlled pressure in an extremity of a compromised patient. Thus, there is a need for a stocking or other compression garment that can be easily put on by a physically compromised patient without application of substantial force to an extremity such as a leg. After application, the garment should conform to the underlying shape of the affected area and apply a controlled and reliable level of pressure. The garment should provide practical long-term service after a reasonable number of applications and washings. Accordingly, what is needed in the art is a new approach that overcomes the deficiencies in the current solutions.

SUMMARY OF THE INVENTION

These and other problems are generally solved or circumvented, and technical advantages are generally achieved, by advantageous embodiments of the present invention, in which a compression garment formed with an electrically stimulated auxetic material and method of forming and operating the same are introduced herein. In one embodiment, the compression garment includes an electrically stimulated auxetic material having a dimension responsive to an electrical signal, an electrical contact coupled to the electrically stimulated auxetic material and an electrical power source. The compression garment also includes a controller, coupled to the electrical contact and the electrical power source, configured to provide the electrical signal to control a pressure produced by the compression garment via the electrically stimulated auxetic material.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, reference is now made to the following descriptions taken in conjunction with the accompanying drawings, in which.

Corresponding numerals and symbols in the different figures generally refer to corresponding parts unless otherwise indicated, and may not be redescribed in the interest of brevity after the first instance. The FIGUREs are drawn to illustrate the relevant aspects of exemplary embodiments.

DETAILED DESCRIPTION OF ILLUSTRATIVE EMBODIMENTS

Figure 1:
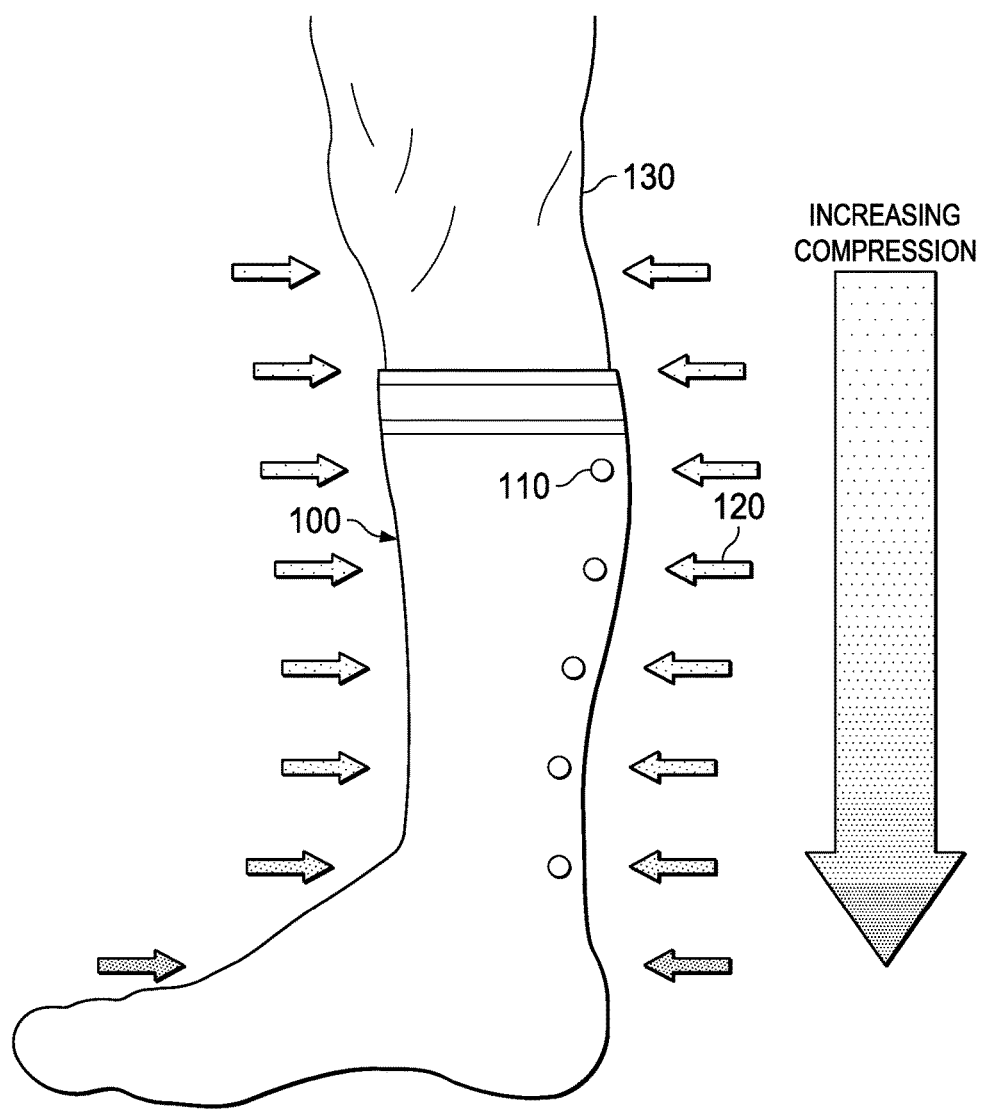
FIG. 1 illustrates a view of an embodiment of a compression garment formed as a stocking.

The making and usage of the present exemplary embodiments are discussed in detail below. It should be appreciated, however, that the embodiments provide many applicable inventive concepts that can be embodied in a wide variety of specific contexts. The specific embodiments discussed are merely illustrative of specific ways to make and use the systems, subsystems and modules associated with a process for producing a compression garment.

An observation was made that a patient standing in water such as a swimming pool experiences an advantageous and well controlled gradient of hydrostatic pressure about the patient's lower extremities (e.g., legs) that promotes venous drainage. In particular, a pressure gradient is produced by the surrounding water from a lower portion of the extremity to a higher portion that substantially balances the ordinary internal pressure gradient of fluids that is induced in the extremity by gravity. A consequence of this observation is that a compression garment should also provide a gradient of pressure along the leg that simulates the pressure gradient produced by an external body of water.

A number of options have been considered for fabrication of a compression garment that can be donned and that produces a reliable level of pressure with a pressure gradient. One option includes the use of sheets formed with nanoparticles. The nanoparticle sheets, however, do not facilitate putting on or removing a stocking that can provide a suitable level of pressure to a patient's lower extremities. Nanoparticle sheets are also impractically expensive from the perspective of widespread use.

Another option that has been considered is the wider use of a wrapped compression bandage, such as an Ace™ bandage, to apply a localized pressure to a limb such as a leg. The bandages, however, are also impractical for long-term use in compromised patients who are generally not able to wrap them in a repeatable manner that produces a reliable pressure level with a suitable pressure gradient.

Thus, an economically practical material is needed that can enable a compression garment constructed therewith to be applied about an affected area of the body, such as a lower portion of a leg, and which can be donned loosely. The resulting garment should be able to be activated to produce a reliable pressure level with a pressure gradient. The resulting garment should be able to be readily deactivated so that it can be removed without difficulty by a patient with compromised facilities.

A further need for a compression garment is for a garment that sequentially and periodically compresses a patient's limb to maintain venous circulation, which is typically a compression garment employed after surgery. A compressive force in such a compression garment is produced by pressurized air produced by an external pump and admitted to the compression garment through a flexible tube. The compression garments are also employed for patients who cannot take a chemical anticoagulant, which may be necessary after a trauma, surgery, or other compromising event.

An air-activated compression garment is typically removably attached to a patient's leg with Velcro straps, and the pressurized air source sequentially and periodically applies a controlled pressure to the leg. A practical difficulty with such arrangements is that it is not practical for the patient to wear the garment regularly, particularly after a few initial applications, which compromises the patient's longer-term treatment. Another difficulty with such arrangements is maintaining an inventory of air pumps in an environment such as a patient care facility of pressurized air sources, which are typically constructed with a small electrically operated pumping arrangement and a controller, and are often tossed out by the facility's cleaning staff.

As introduced herein, a washable compression garment is constructed from electrically stimulated auxetic material (e.g., an auxetic yarn), a dimension (e.g., a length) of which is responsive to an electrical signal, such as an electrical signal applied from end to end. An example of an auxetic material is Zetix™ helical-auxetic fiber technology, developed by Auxetics Technologies, Ltd. The length of the electrically stimulated auxetic material is responsive to the electrical signal, such as an applied controllable dc voltage, or a train of electrical pulses with controllable pulse width and/or pulse amplitude. An auxetic material is a material that generally expands diametrically when a lengthwise mechanical force is applied thereto. An electrically stimulated auxetic material is a material that expands diametrically or in thickness along a length thereof when an electrical signal is applied thereto.

Turning now to FIG. 1, illustrated is a view of an embodiment of a compression garment 100 formed as a stocking that is applied over a leg 130 and foot of a patient. The compression garment 100 is formed with a tighter weave in a lower portion than in an upper portion to produce a pressure gradient illustrated by the arrows 120 when the compression garment is applied to the leg 130 of the patient. The compression garment is formed with sensors (e.g., a pressure sensor, one of which is designated 110) to provide one or more feedback signals to a controller (not shown in FIG. 1) to enable the controller to control pressure in the compression garment.

Figure 2:
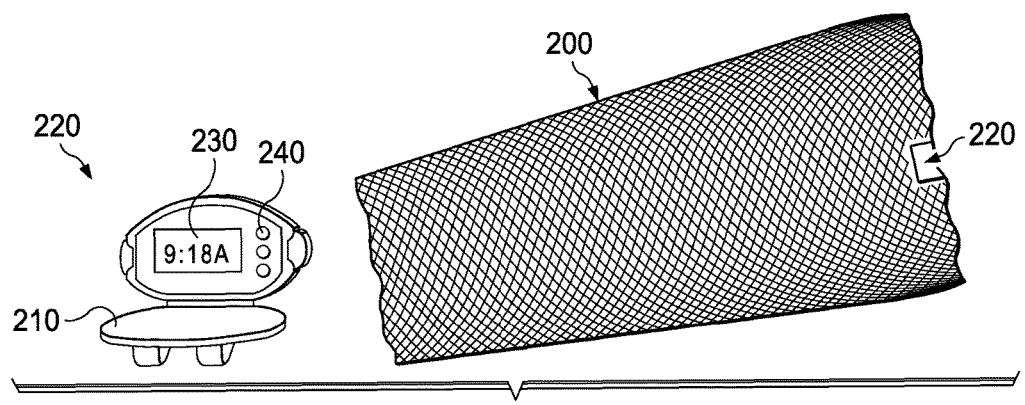
FIG. 2 illustrates a view of an embodiment of a compression garment formed as a sleeve.

Turning now to FIG. 2, illustrated is a view of an embodiment of a compression garment 200 formed as a sleeve to be pulled over an arm or head of a patient. A controller 220 (and an electrical power source, see FIG. 3) is removably attached by a clip 210 to the compression garment 200 and provides a visual indication of performance data of the compression garment via a display (e.g., a liquid crystal display) 230. The display 230 includes buttons, such as button 240, to enable the controller 220 to be reprogrammed to acquire particular performance data or to reprogram the controller 220, for example, to adapt a pressure produced by the compression garment 200 to a particular patient.

As mentioned above, the compression garment 200 can also be applied with suitable design to the face or to the arms of a patient. The compression garment 200 can be constructed with a tighter weave in one portion than in another portion to produce a pressure gradient over an affected area when an electrical signal is applied thereto.

Figure 3:
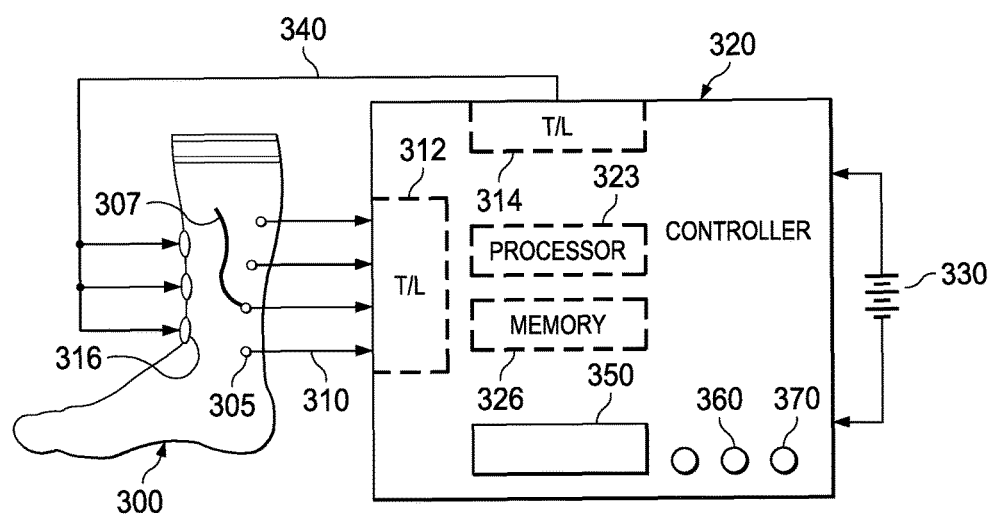
FIG. 3 illustrates a view of an embodiment of a compression garment formed as a stocking including sensors coupled to a controller.

Turning now to FIG. 3, illustrated is a view of an embodiment of a compression garment 300 formed as a stocking including sensors (e.g., a pressure sensor, ones of which are designated 305, 307) coupled by leads (one of which is designated 310) to a controller 320 via a terminal ("T/L") 312. The controller 320 in turn is coupled to an electrical power source such as the battery 330 to power the components thereof including a processor 323 and memory 326. The processor 323 and memory 326 cooperate to perform the functions of the controller 320 as set forth herein. The controller 320 provides an electrical signal(s) over a lead(s) 340 from the controller 320 (via a terminal 314) to electrical contacts (one of which is designated 316) of the compression garment 300. The controller 320 is fitted with a display 350 to provide a visual indication of performance data (e.g., recorded in the memory 326 by the processor 323). The controller 320 includes buttons, such as button or external switch 360 to enable the processor 323 to be reprogrammed or to acquire particular performance data as described herein. The controller 320 also includes an alarm indicator 370 to provide an indication of a pressure alarm condition or other failure mechanism. An indication of a pressure alarm condition or other failure mechanism may be provided when the pressure of the compression garment is relieved.

The pressure applied by the compression garment 300 to the patient's affected area is controlled by the controller 320. The sensors 305, 307 provide in vivo signals over the leads 310 to the controller 320 for certifiably monitoring and controlling pressure applied by the compression garment 300. In response thereto, the controller 320 provides the electrical signal over the lead 340 coupled to the compression garment 300 to control the pressure applied to the patient's affected area. The electrical signal(s) from the controller 320 over the lead 340 may be as an electrical wave of pressure to the electrical contacts 316 of the compression garment. The controller 320 is configured to increase or decrease a voltage applied to the compression garment 300 or a duty cycle or amplitude of a pulse to adapt to the needs of an individual patient.

In an embodiment, the pressure is sensed (via the sensors 305, 307) at one or a plurality of locations to provide the feedback signal or signals. The multiple electrical connections over the leads 310 may be made to the compression garment 300 to apply and control pressure in different regions thereof. The sensors can be formed with an optical fiber (see, e.g., the sensor designated 307) woven into the material, for example, as described by Wang et al. in the paper entitled "An Optical Fiber Bragg Grating Force Sensor for Monitoring Sub-Bandage Pressure During Compression Therapy," published Aug. 15, 2013, which is incorporated herein by reference.

The sensors 305, 307 provide a mechanism that can be employed to assess reliability and performance of the compression garment 300. A warning signal produced by the alarm indicator (e.g., a light-emitting diode) 370 may be employed to signal that the compression garment 300 has lost an ability to produce an intended pressure. Again, substantially the entire pressure of the compression garment 300 may be relieved to provide the warning signal when a suitable pressure level cannot be maintained.

The controller 320 can also be employed to provide an indication of time, such as a cumulative application time on the display 350 that the compression garment 300 has been worn, or other performance data. The controller 320 can be employed to provide data for a physician to monitor and assess conformity of use by a patient.

The pressure produced by the compression garment 300 can be static and graduated along the length thereof, or it can be dynamic in the sense that the compression garment 300 periodically applies pressure, and/or produces a progressive wave of compression along the length of an extremity such as produced by a massage. The pressure can be produced in peristaltic waves to induce movement of fluid within the patient's limb. The controller 320 can also be employed to periodically cycle pressure in the compression garment 300 on and off. Thus, a progressive pressure can be applied to provide a massaging action to an affected area of a patient in conjunction with the electrical signal(s) from the controller 320.

The controller 320 is configured to be programmable so that it is capable of changing pressure level to provide an altered level of treatment over time for a patient. The controller 320 is capable of alternating between static and dynamic pressure operation of the compression garment 300. The programmability can be performed with the button 360 of the controller 320. In a further application, the process of constructing a compression garment 300 is employed to construct clothing to provide a fashionable appearance for a wearer, such as an easily put on shrink-to-fit garment.

In an embodiment, the compression garment 300 is washable and can be easily donned loose, and then have a conformity changed to that of underlying contours of the patient's affected area such as the patient's leg. The compression garment 300 will generate sufficient treatment pressures in a gradient up the leg or other extremity and, when turned off, becomes loose and easily removed without aggravating an underlying wound. The compression garment 300 can be easily transported to a patient's home from a patient-care facility, and operated with reliably controlled and monitored pressure that forms a pressure gradient along a lower extremity. The compression garment 300 is removably coupled to the controller 320 and the battery 330 that in turn can be removably attached to the patient's body such as by a small strap. Akin to the compression garment 200 illustrated in FIG. 2, the battery 330 and the controller 320 are removably coupled to the compression garment 300 to enable the compression garment 300 to be washed detached from the battery 330 and the controller 320.

The compression garment 300 is formed with an electrically stimulated auxetic material (e.g., auxetic yarn) that can be electrically conductive and can be extended or contracted (to alter a diameter thereof) or a thickness thereof can be increased or decreased by application of the electrical signal. A dimension (e.g., diameter or a thickness along a length thereof) of the electrically stimulated auxetic material is responsive to the electrical signals. A mechanical response of the electrically stimulated auxetic material can be such that application of the electrical signal shortens the auxetic material from its relaxed state to produce a compressive pressure in the compression garment 300. In the relaxed state, the compression garment 300 is easily pulled over a limb or other affected area by the patient. The electrical signal is then applied substantially continuously to produce a compressive pressure. A thickness of an electrically stimulated auxetic material can increase or decrease upon application or removal of the electrical signal.

In an embodiment, application of a non-zero electrical signal such as a dc signal of a few volts lengthens the electrically stimulated auxetic material so that a pressure of the compression garment 300 is relieved and the compression garment 300 can be removed by the patient when the electrical signal is applied. When the electrical signal is removed, the compression garment 300 produces a tightening gradient of pressure to an extremity such as a leg. The arrangement would not drain power from the battery 330 during ordinary wearing of the compression garment 300.

Figures 4, 5:
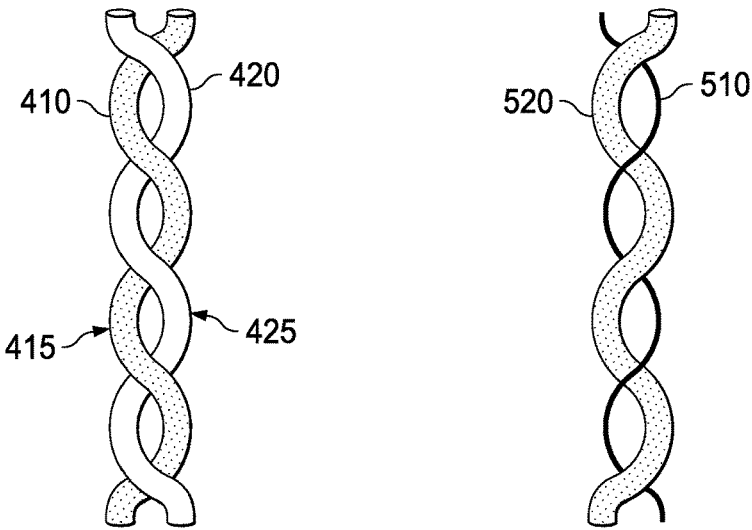
FIG. 4 illustrates a view of an embodiment of an electrically stimulated auxetic material formed with a sandwiched arrangement of dissimilar materials.
FIG. 5 illustrates a view of an embodiment of an antimicrobial thread that can be wound together or otherwise integrated with an electrically stimulated auxetic material that can be employed to form a weave of a compression garment.

Turning now to FIG. 4, illustrated is a view of an embodiment of an electrically stimulated auxetic material (e.g., an auxetic yarn) formed with a sandwiched arrangement of first and second dissimilar materials 410, 420. The first and second dissimilar materials 410, 420 such as materials made from electroconductive polymers (e.g., woven fabric of polyacrylonitrile staple fibres and woven threads of polyamide with a silver coating) are selected so that one has a higher electrode potential than the other, thereby forming a battery. An outer coating of one or both of the first and second dissimilar materials 410, 420 (e.g., an outer coating 415 for the first dissimilar material 410 and an outer coating 425 for the first dissimilar material 420) is selected to provide a battery cell separator function therebetween so that an electromotive potential is produced between the first and second dissimilar materials 410, 420. Thus, the electrically stimulated auxetic material employed as a weaving component for construction of a compression garment is formed with a sandwiched arrangement of the first and second dissimilar materials 410, 420 so that a voltage is produced between terminals coupled thereto that produces an electrical source of power for the electrically stimulated auxetic material. The electrical source of power can be employed to activate the electrically stimulated auxetic material and for other elements associated with the compression garment such as a controller (including in a processor), a pressure sensor and an alarm indicator.

Turning now to FIG. 5, illustrated is a view of an embodiment of an antimicrobial thread 510 that can be wound together or otherwise integrated with an electrically stimulated auxetic material 520 that can be employed to form a weave of a compression garment. The integral antimicrobial thread 510 can reduce a likelihood of infection. The antimicrobial thread 510 can be formed, without limitation, with fine wires of copper or silver.

Figure 6:
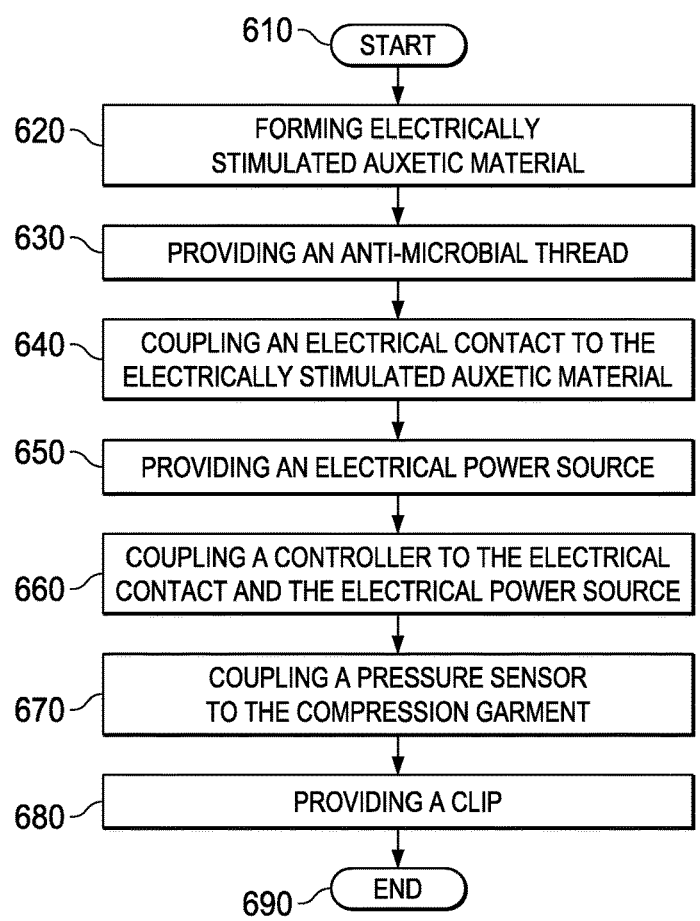
FIG. 6 illustrates a flow diagram of an embodiment of forming a compression garment.

Turning now to FIG. 6, illustrated is a flow diagram of an embodiment of forming a compression garment. The method begins in a start step or module 610. In a step or module 620, an electrically stimulated auxetic material is formed having a dimension responsive to an electrical signal. The compression garment may be formed with a tighter weave in one portion than in another portion to produce a pressure gradient when the compression garment is applied to a patient. Additionally, the electrically stimulated auxetic material may include a sandwiched arrangement of dissimilar materials. In a step or module 630, an antimicrobial thread is weaved into the compression garment.

The method continues with coupling an electrical contact to the electrically stimulated auxetic material in a step or module 640 and providing an electrical power source in a step or module 650. In a step or module 660, a controller is coupled to the electrical contact and the electrical power source. The controller including a processor and memory is configured to provide or produce the electrical signal to control a pressure produced by the compression garment via the electrically stimulated auxetic material. The processor is configured to record in the memory performance data of the compression garment. The method continues with coupling a pressure sensor to the compression garment configured to provide or produce a feedback signal for the controller to control the pressure produced by the compression garment in a step or module 670. In a step or module 680, a clip is provided to attach the controller and the electrical power source to the compression garment. The method ends in an end step or module 690.

Thus, a compression garment formed with an electrically stimulated auxetic material (e.g., auxetic yarn) has been introduced herein. In one embodiment, the compression garment includes pressure sensors and a controller including a processor to control a pressure produced by the compression garment. The controller is coupled to an electrical power source such as a battery. The battery can be formed as a yarn electrodes of which are formed by a sandwiched arrangement of dissimilar threads.

The controller or related method of operating the same may be implemented as hardware (embodied in one or more chips including an integrated circuit such as an application specific integrated circuit), or may be implemented as software or firmware for execution by a processor (e.g., a digital signal processor) in accordance with memory. In particular, in the case of firmware or software, the exemplary embodiment can be provided as a computer program product including a computer readable medium embodying computer program code (i.e., software or firmware) thereon for execution by the processor.

Program or code segments making up the various embodiments may be stored in the computer readable medium. For instance, a computer program product including a program code stored in a computer readable medium (e.g., a non-transitory computer readable medium) may form various embodiments. The "computer readable medium" may include any medium that can store or transfer information. Examples of the computer readable medium include an electronic circuit, a semiconductor memory device, a read only memory ("ROM"), a flash memory, an erasable ROM ("EROM"), a floppy diskette, a compact disk ("CD")-ROM, and the like.

As described above, the exemplary embodiment provides both a method and corresponding systems consisting of various modules providing functionality for performing the steps of the method. Although the embodiments and its advantages have been described in detail, it should be understood that various changes, substitutions, and alterations can be made herein without departing from the conceptual spirit and scope thereof as defined by the appended claims. Also, many of the features, functions, and steps of operating the same may be reordered, omitted, added, etc., and still fall within the broad scope of the various embodiments.

Moreover, the scope of the various embodiments is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized as well. Accordingly, the appended claims are intended to include within their scope such processes, machines, manufacture, compositions of matter, means, methods, or steps.

What is claimed is:

1. A compression garment, comprising:
an electrically stimulated auxetic material comprising a first material, a second material helically wrapped around the first material, and a dimension responsive to an electrical signal conducted through the first material of the electrically stimulated auxetic material;
an electrical contact coupled to said electrically stimulated-auxetic material;
an electrical power source; and
a controller, coupled to said electrical contact and said electrical power source, configured to provide said electrical signal to be conducted through the first material of the electrically stimulated auxetic material in order to control and generate a pressure to be applied to a user by the electrically stimulated auxetic material in response to the electrical signal being conducted through first material of the electrically stimulated auxetic material.

2. The compression garment as recited in claim 1 wherein said controller and said electrical power source are removably attachable from said compression garment.

3. The compression garment as recited in claim 1 further comprising a pressure sensor coupled to said compression garment configured to provide a feedback signal for said controller to control said pressure to be applied to a user by said compression garment.

4. The compression garment as recited in claim 3 wherein said pressure sensor comprises an optical fiber woven into said compression garment.

5. The compression garment as recited in claim 1 wherein said controller comprises a processor configured to provide said electrical signal as an electrical wave of pressure in said compression garment.

6. The compression garment as recited in claim 1 wherein said controller comprises a processor configured to be reprogrammable by an external switch.

7. The compression garment as recited in claim 1 wherein said controller comprises a processor configured to record in memory performance data of said compression garment.

8. The compression garment as recited in claim 1 wherein said controller is configured to periodically cycle pressure of said compression garment via said electrical signal.

9. The compression garment as recited in claim 1 wherein said compression garment is formed with a tighter weave in one portion than in another portion to produce a pressure gradient of the compression garment on the user in response to the an electrical signal being applied to the compression garment.

10. The compression garment as recited in claim 1 wherein said compression garment comprises an antimicrobial thread.

11. The compression garment as recited in claim 1 wherein said pressure is relieved by application of a nonzero value of said electrical signal being conducted through the electrically stimulated auxetic material.

12. The compression garment as recited in claim 1 wherein an indication of a pressure alarm condition for said compression garment is provided when said pressure of said compression garment is relieved.

13. The compression garment as recited in claim 1 wherein said electrically stimulated-auxetic material comprises a sandwiched arrangement of dissimilar materials.

14. A method of forming a compression garment, comprising steps of:
forming an electrically stimulated auxetic material comprising a first material, a second material helically wrapped around the first material, and a dimension responsive to an electrical signal conducted through the first material of the electrically stimulated auxetic material;
coupling an electrical contact to said electrically stimulated auxetic material;
providing an electrical power source; and
coupling a controller to said electrical contact and said electrical power source, said controller configured to provide said electrical signal to be conducted through the first material of the electrically stimulated auxetic material in order to control and generate a pressure to be applied to a user by the electrically stimulated auxetic material in response to the electrical signal being conducted through first material of the electrically stimulated auxetic material.

15. The method as recited in claim 14 further comprising providing a clip to attach said controller and said electrical power source to said compression garment.

16. The method as recited in claim 14 further comprising coupling a pressure sensor to said compression garment configured to provide a feedback signal for said controller to control said pressure to be applied to a user by said compression garment.

17. The method as recited in claim 14 wherein said controller comprises a processor configured to record in memory performance data of said compression garment.

18. The method as recited in claim 14 wherein said compression garment is formed with a tighter weave in one portion than in another portion to produce a pressure gradient when said compression garment is applied to the user.

19. A compression garment, comprising:
an electrically stimulated auxetic yarn comprising a first material and a second material, where the first material is an electroconductive polymer with a higher electrode potential than the second material, where an electromotive potential is produced between the first and second dissimilar materials in response to an electrical signal being conducted through the electrically stimulated auxetic yarn;
an electrical contact coupled to the electrically stimulated auxetic yarn;
an electrical power source; and
a controller, coupled to the electrical contact and the electrical power source, configured to provide the electrical signal to control a pressure to be applied to a user by the compression garment via the electrically stimulated auxetic yarn.

20. The compression garment of claim 19, wherein:
the first material is a polyacrylonitrile staple fiber;
the second material is a thread of polyamide with a silver coating;
wherein the first material and second material are wound around each other about an axis that runs parallel to the longest dimension of both the first material and the second material.

* * * * *